(12) United States Patent
Bruns et al.

(10) Patent No.: US 7,084,137 B2
(45) Date of Patent: Aug. 1, 2006

(54) THIAZINES AND THIAZOLES AS AGENTS FOR PROTECTING MATERIALS

(75) Inventors: Rainer Bruns, Leverkusen (DE); Hermann Uhr, Leverkusen (DE); Martin Kugler, Leichlingen (DE); Peter Wachtler, Krefeld (DE); Oliver Kretschik, Köln (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/835,224

(22) Filed: Apr. 29, 2004

(65) Prior Publication Data

US 2004/0204405 A1 Oct. 14, 2004

Related U.S. Application Data

(62) Division of application No. 10/178,134, filed on Jun. 24, 2002, now abandoned.

(30) Foreign Application Priority Data

Jun. 26, 2001 (DE) .................................. 101 30 706

(51) Int. Cl.
C07D 279/06 (2006.01)
A61K 31/54 (2006.01)
A61K 31/541 (2006.01)

(52) U.S. Cl. ...................................... 514/227.2; 544/55

(58) Field of Classification Search .................. 544/55; 514/227.2
See application file for complete search history.

(56) References Cited

U.S. PATENT DOCUMENTS

| 3,131,183 A | * | 4/1964 | Hoffman et al. ............... 544/54 |
| 3,178,425 A | * | 4/1965 | Hoffman et al. ............... 544/53 |
| 3,546,235 A | | 12/1970 | Bader et al. ............. 260/294.8 |
| 3,651,234 A | | 3/1972 | Bader et al. ................. 424/277 |
| 3,712,908 A | | 1/1973 | Bader et al. ............ 260/327 C |
| 4,097,669 A | | 6/1978 | Reisdorff et al. ........... 542/413 |
| 4,131,608 A | | 12/1978 | Zirngibl et al. ......... 260/307 D |
| 4,324,793 A | | 4/1982 | Hagen et al. ................ 424/270 |
| 4,584,305 A | | 4/1986 | Brugmanns et al. ........ 514/368 |

FOREIGN PATENT DOCUMENTS

| DE | 35 39 476 | 5/1987 |
| EP | 0 040 310 | 11/1981 |
| EP | 0 299 694 | 1/1989 |
| EP | 0 545 103 | 6/1993 |
| GB | 1 379 754 | 1/1975 |
| GB | 1 511 390 | 5/1978 |
| GB | 2 052 481 | 1/1981 |
| JP | 54145680 | * 11/1979 |
| JP | 11140063 | * 5/1999 |

OTHER PUBLICATIONS

Synthetic Commun., 5(2), (month unavailable) 1975, "The Formation of 2-Substituted-2-Thiazolines And 5,6-Dihydro-(4H)-1,3-Thiazines from Haloalkylisothiocyanates", R.E. Hackler and T.W. Balko.

Database Caplus 'Online! Chemical Abstracts Service, Columbus, Ohio, US; Muthusubramanian et al: "Convenient synthesis of thiocyanomethylthio heteroaromatics as antifungal agents" Database accession No. 1998: 395793 XP002210625 CAS-RN 210532-90-4.

Database Caplus 'Online! Chemical Abstracts Service, Columbus, Ohio, US; Rani et al.: "Thiazoline analogs of epiderstatin, new inhibitors of cell cylce of tdFT-21 cells" Database Accession No. 1995:897719, XP002210626, CAS-RN 171598-79-1, 171598-80-4, 171598-81-5, 171598-82-6, 171522-76-2, 171598-77-9.

Database Caplus 'Online! Chemical Abstracts Service, Columbus, Ohio, US; Comby et al: "Antibacterial, antiparasitic and antifungal sulfonamides derived from imidazole: estimation of antithyroid effects in the rat" Database accession No. 1994:153466 XP002210627 CAS-RN 96-53-7.

Database Caplus 'Online! Chemical Abstracts Service, Columbus, Ohio, US; Ternanski RJ et al: "Discovery and structure-activity relationship of a series of 1-catrba-1dethiacephems exhibiting activity against methicillin-resistant *Staphylococcus aureus*" Database accession No. 1993: 117001 XP002210628 CAS-RN 141178-74-5, 149-40-1.

Database Caplus 'Online! Chemical Abstracts Service, Columbus, Ohio, US; Terachi et al: "Preparation of succinimides as agrochemical fungicides for Phytophtora and Puccinica control" Database accession No. 1990:510914 XP002210629 CAS-RN 122419-79-8.

(Continued)

Primary Examiner—Venkataraman Balasubramanian
(74) Attorney, Agent, or Firm—Jill Denesvich

(57) ABSTRACT

The novel and known thiazines and thiazoles of the formula (I)

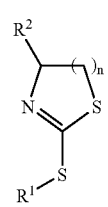

in which
$R^1$, $R^2$ and n are as defined in the description, are highly suitable for use as biocides for protecting industrial materials.

9 Claims, No Drawings

OTHER PUBLICATIONS

Database Caplus 'Online! Chemical Abstracts Service of, Columbus, Ohio, US; Hirose et al: "Oxonaphthridine- and oxoquinolin-3-carboxylic acid as microbicides" Database accession No. 1990:20980 XP02210630 CAS-RN 124256-13-9.

Database Caplus 'Online! Chemical Abstracts Service, Columbus, Ohio, US; Yamashita et al: "2-substituted thioazoline derivatives" Database accession No. 1986;168454 XP002210631 CAS-RN 2571-74-2, 19975-56-5, 23994-89-0, 41834-62-2, 50668-02-5, 100498-90-6, 100498-91-7, 100498-92-8, 100498-93-9, 100498-94-0.

Database Caplus 'Online! Chemical Abstracts Service, Columbus, Ohio, US; Nihon Tokushu Noyaku Seizo KK: "Benzisothiazole compounds" Database accession No. 1982:142839 XP002210632 CAS-RN 81218-73-7.

Database Caplus 'Online! Chemical Abstracts Service, Columbus, Ohio, US; Abdel-Lateef et al.: "Systemic and chemotherapeutic fungicidal activity-chemical structure relation of some 4-methyl—5-thiazolecarboxylic acid derivatives" Database accession No. 1974:515750 XP002210633 CAS-RN 53040-06-5.

Database Caplus 'Online! Chemical Abstracts Service, Columbus, OH, US; Tsymbal et al.: "Anti-Ustilaginacea activity of some chemical compounds" Database accession No. 1968:451135 XP002210634 CAS-RN 1437-88-3.

Database Caplus 'Online! Chemical Abstracts Service, Columbus, Ohio, US; Reisdorff et al.: "2-substituted 5-(trifluoromethyl)-1, 3, 4-thiadiazoles as antiparasitic agents" Database accession No. 1977:171462 XP002210635 CAS-RN 62655-49-6.

Database Caplus 'Online! Chemical Abstracts Service, Columbus, Ohio, US; Han et al.: "Synthesis and fungicidal activity of substituted arylimonothiazolines" Database accession No. 2000:813766 XP00221636 CAS-RN 3571-74-2.

Database Chemcats 'Online! Chemical Abstract Online; 21. Januar 2002 (Jan. 21, 2002) Ambiter: "Exploratory library 66839 (CAS 438481-76-6)" Database accession No. 2002:2834310 XP002211695.

Database WPI Week 197719 Derwent Publications Ltd., London, GB; AN 1977-33719Y XP002210637 & JP 52 041235 A (Ajinimoto KK), 30. Marz 1977 (Mar. 30, 1977) Form. (III).

Database WPI Week 199954 Derwent Publications Ltd., London, GB; AN 1999-633815 XP002210638 & WO 99 52874 A (Ube Ind Ltd), Oktober 1999 (Oct. 21, 1999) Zeile 18; Beispliele 17-1.

* cited by examiner

THIAZINES AND THIAZOLES AS AGENTS FOR PROTECTING MATERIALS

This application is a Divisional of Ser. No. 10/178,134 filed Jun. 24, 2002 now abandoned.

BACKGROUND

The present invention relates to novel thiazines and novel thiazoles, to processes for their preparation, to novel mixtures of thiazines and/or thiazoles with other agents for protecting materials and to the use of novel and known thiazines and novel and known thiazoles as microbicides for protecting industrial materials.

Certain thiazines and thiazoles and processes for their preparation are already known from the literature (cf. R. E. Hackler et al., Synthetic Commun., 1975, 5, 143–146). It is furthermore known that some thiazines can be used as fungicides in agriculture and horticulture (cf. JP-A-2000-119263). U.S. Pat. No. 4,584,305 discloses that some thiazoles have nematicidal action.

However, these known thiazines and thiazoles have not been described as agents for protecting materials.

Surprisingly, it has now been found that the novel and known thiazines and thiazoles of the general formula (I) are particularly suitable for protecting industrial materials against attack by microorganisms.

SUMMARY

The invention relates to a method comprising treating an industrial material with a compound of the formula (I)

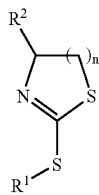

(I)

wherein $R^1$ represents hydrogen or in each case optionally substituted alkyl, alkenyl, alkinyl, cycloalkyl, aryl or heterocyclcl, $R^2$ represents hydrogen, alkoxycarbonyl or alkylcarbonyl and n represents 1 or 2, and thereby protecting the industrial material.

The invention also relates to a compound of the formula (I)

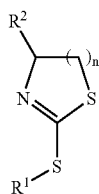

(I)

wherein $R^1$ represents hydrogen or in each case optionally substituted alkyl, alkenyl, alkinyl, cycloalkyl, aryl or heterocyclyl, $R^2$ represents hydrogen, alkoxycarbonyl or alkylcarbonyl and n represents 1 or 2, except for 2-(phenylsulfanyl)-5,6-dihydro-4H-1,3-thiazine,
CAS No. [73122-32-4]

2-[(3-chlorophenyl)sulfanyl]-5,6-dihydro4H-1,3-thiazine,
CAS No. [73122-33-5]

2-[(4-chlorophenyl)sulfanyl]-5,6-dihydro-4H-1,3-thiazine,
CAS No. [10554-28-6]

2-(methylsulfanyl)-5,6-dihydro-4H-1,3-thiazine,
CAS No. [58842-19-6]

2-[(4-methoxyphenyl)sulfanyl]-5,6-dihydro-4H-1,3-thiazine,
CAS No. [73122-49-3]

2-[(4-methylphenyl)sulfanyl]-5,6-dihydro4H-1,3-thiazine,
CAS No. [73122-44-8]

2-(ethylsulfanyl)-5,6-dihydro-4H-1,3-thiazine, Beilstein reference No. [4-27-00-01718]

2-[(4-nitrophenyl)sulfanyl]-5,6-dihydro-4H-1,3-thiazine,
CAS No. [73122-52-8]

2-[(3,4-dichlorophenyl)sulfanyl]-5,6-dihydro-4H-1,3-thiazine,
CAS No. [73122-34-6]

2-[(2-chlorophenyl)sulfanyl]-5,6-dihydro-4H-1,3-thiazine,
CAS No. [55545-14-7]

2-(5,6-dihydro-4H-1,3-thiazin-2-ylsulfanyl)-1-phenylethanone,
CAS-No. [88636-60-6]

2-{[3-(trifluoromethyl)-1,2,4-thiadiazol-5-yl]sulfanyl}-5,6-dihydro-4H-1,3-thiazine, CAS No. [62655-49-6]

2-[(2,4-dichlorophenyl)sulfanyl]-5,6-dihydro-4H-1,3-thiazine,
CAS No. [73122-35-7]

2-[(4-bromophenyl)sulfanyl]-5,6-dihydro-4H-1,3-thiazine,
CAS No. [73122-41-5]

2-[(2,6-dichlorophenyl)sulfanyl]-5,6-dihydro4H-1,3-thiazine,
CAS No. [73122-36-8]

2-[(3,5-dichlorophenyl)sulfanyl]-5,6-dihydro-4H-1,3-thiazine,
CAS No. [73122-37-9]

2-[(3-methylphenyl)sulfanyl]-5,6-dihydro4H-1,3-thiazine,
CAS No. [73122-45-9]

2-[(2-methylphenyl)sulfanyl]-5,6-dihydro-4H-1,3-thiazine,
CAS No. [73122-46-0]

4-(5,6-dihydro-4H-1,3-thiazin-2-ylsulfanyl)-N,N-dimethylaniline,
CAS No. [73122-51-7]

2-[(4-fluorophenyl)sulfanyl]-5,6-dihydro-4H-1,3-thiazine,
CAS No. [73122-42-6]

methyl 2-(methylsulfanyl)-4,5-dihydro-1,3-thiazole4-carboxylate,
CAS No. [117389-66-9]

methyl 2-(4-chlorobenzylsulfanyl)-4,5-dihydro-1,3-thiazole4-carboxylate,
CAS No. [117389-75-0]

methyl 2-(benzylsulfanyl)-4,5-dihydro-1,3-thiazole-4-carboxylate,
CAS No. [117389-66-9]

2-[(2-methyl-2-propenyl)sulfanyl]-4,5-dihydro-1,3-thiazole,
CAS No. [56502-83-1]

2-[benzylsulfanyl]-4,5-dihydro-1,3-thiazole,
CAS No. [41834-62-2]
2-[(2-methylpropyl)sulfanyl]-4,5-dihydro-1,3-thiazole,
Beilstein reference No. [1099990]
2-[allylsulfanyl]-4,5-dihydro-1,3-thiazole,
CAS No. [3571-74-2]
2-[4-nitrophenylsulfanyl]-4,5-dihydro-1,3-thiazole,
CAS No. [103482-99-1]
2-[4-methoxyphenylsulfanyl]-4,5-dihydro-1,3-thiazole,
CAS No. [13094-98-9]
2-[4-chlorophenylsulfanyl]-4,5-dihydro-1,3-thiazole,
CAS No. [103482-92-4]
2-[2-chlorophenylsulfanyl]-4,5-dihydro-1,3-thiazole,
CAS No. [55545-15-8]
2-[3-chlorophenylsulfanyl]-4,5-dihydro-1,3-thiazole,
CAS No. [103482-93-5]
2-(4,5-dihydro-1,3-thiazol-2-ylsulfanyl)-1-phenylethanone,
CAS No. [17385-78-3]
2-[methylsulfanyl]-4,5-dihydro-1,3-thiazole,
CAS No. [19975-56-5]
2-{[(4,5-dihydro-1,3-thiazol-2-ylsulfanyl)methyl]sulfanyl}-4,5-dihydro-1,3-thiazole, CAS No. [89943-80-6]
2-[phenylsulfanyl]-4,5-dihydro-1,3-thiazole,
CAS No. [62652-38-4],
2-[(4-tert-butylphenyl)sulfanyl]-5,6-dihydro-4H-1,3-thiazine
CAS No. [73122-48-2]
2-[(4-chloro-2-methylphenyl)sulfanyl]-5,6-dihydro-4H-1,3-thiazine
CAS No. [73122-47-1]
2-[(pentachlorophenyl)sulfanyl]-5,6-dihydro-4H-1,3-thiazine
CAS No. [73122-40-4]
2-[(2,4,6-trichlorophenyl)sulfanyl]-5,6-dihydro-4H-1,3-thiazine
CAS No. [73122-39-1]
2-[(2,5-dichlorophenyl)sulfanyl]-5,6-dihydro-4H-1,3-thiazine
CAS No. [73122-38-0].

The invention also relates to a method for protecting an industrial material against attack and/or destruction by an micro-organisms, characterised in that at least one compound of the formula (I) comprising placing a compound of formula (I) on the organism or the habitat of the organism, and (b) allowing the compound of formula (I) to act on the micro-organism or its habitat.

The invention relates to a microbicidal composition for protecting industrial material, comprising at least one compound of a compound of the formula (I)

wherein $R^1$ represents hydrogen or in each case optionally substituted alkyl, alkenyl, alkinyl, cycloalkyl, aryl or heterocyclyl, $R^2$ represents hydrogen, alkoxycarbonyl or alkylcarbonyl and n represents 1 or 2, and at least one solvent or diluent.

The invention also relates to an industrial material comprising an industrial material with a compound of the formula (I)

wherein $R^1$ represents hydrogen or in each case optionally substituted alkyl, alkenyl, alkinyl, cycloalkyl, aryl or heterocyclyl,
$R^2$ represents hydrogen, alkoxycarbonyl or alkylcarbonyl and
n represents 1 or 2. These and other features, aspects, and advantages of the present invention will become better understood with reference to the following description and appended claims.

DESCRIPTION

The present invention provides the use of novel and known compounds of the general formula (I)

in which
$R^1$ represents hydrogen or in each case optionally substituted alkyl, alkenyl, alkinyl, cycloalkyl, aryl or heterocyclyl,
$R^2$ represents hydrogen, alkoxycarbonyl or alkylcarbonyl and
n represents 1 or 2, their metal salts and acid addition compounds as biocides for protecting industrial materials.

For the purpose of the present invention, the alkyl radicals mentioned are, including in the meaning of alkylcarbonyl, in each case straight-chain or branched and unsubstituted or substituted and contain 1 to 12 carbon atoms, in particular 1 to 8 carbon atoms. Preferred alkyl radicals are methyl, ethyl, propyl, butyl and octyl. The alkenyl and alkinyl radicals mentioned are in each case straight-chain or branched, and unsubstituted or substituted and contain 2 to 6 carbon atoms, in particular 2 to 4 carbon atoms. Preference is given to propenyl and butinyl. Cycloalkyl generally represents an unsubstituted or substituted cycloalkyl radical having 3 to 8 carbon atoms, in particular 3 to 6 carbon atoms. Preference is given to cyclopropyl and cyclopentyl. The alkoxy radicals mentioned in the meaning of alkoxycarbonyl are in each case straight-chain or branched and unsubstituted or substituted and contain 1 to 6 carbon atoms, in particular 1 to 3 carbon atoms. Preference is given to methoxy and ethoxy. Aryl generally represents an unsubstituted or substituted 6- to 10-membered aromatic radical, in particular phenyl.

Halogen generally represents fluorine, chlorine, bromine or iodine, in particular fluorine, chlorine and bromine. Heterocyclyl generally represents a saturated mono- or polyunsaturated or aromatic 5- to 7-membered ring, in particular 5- or 6-membered ring, having one or more identical or different heteroatoms, in particular 1 to 4 heteroatoms and preferably 1 to 3 heteroatoms, from the group consisting of N, O and S, preferably N and S, optionally with a further fused-on carbocyclic ring, in particular a 6-membered carbocyclic ring, preferably a 6-membered aromatic ring.

The above-mentioned radicals are in each case optionally mono- to polysubstituted, in particular mono- to trisubstituted, preferably mono- or disubstituted, by identical or different substituents, possible substituents being in each case: halogen, alkyl, cycloalkyl, haloalkyl, alkoxy, haloalkoxy, hydroxyl, nitro, nitrile, amino, dialkylamino, carbonyl, phenyl, phenoxy, sulfanylthiazolyl or sulfanylthiazinyl.

Preference is given to compounds of the formula (I) in which $R^1$ represents hydrogen or represents $C_1$–$C_{12}$-alkyl which is optionally mono- or polysubstituted by identical or different substituents from the group consisting of $C_1$–$C_6$-alkoxy; $C_1$–$C_6$-alkoxycarbonyl; in each case optionally halogen- and/or $C_1$–$C_6$-alkoxy-substituted phenyl or phenylcarbonyl; $C_1$–$C_6$-alkylcarbonyl; optionally halogen-substituted $C_3$–$C_8$-cycloalkylcarbonyl; 5- or 6-membered heterocyclylcarbonyl having 1 to 3 heteroatoms from the group consisting of N, O and S; 5- or 6-membered heterocyclylthio having 1 to 3 heteroatoms from the group consisting of N, O and S; or represents $C_2$–$C_6$-alkenyl, $C_2$–$C_6$-alkinyl, $C_3$–$C_8$-cycloalkyl or represents phenyl which is optionally mono- or polysubstituted by identical or different substituents from the group consisting of halogen, $C_1$–$C_6$-alkyl, $C_3$–$C_8$-cycloalkyl, $C_1$–$C_6$-haloalkyl, $C_1$–$C_6$-haloalkoxy, $C_1$–$C_6$-alkoxy, nitro, nitrile, hydroxyl, amino, phenoxy, phenyl and di-$C_1$–$C_6$-alkylamino, or represents a 5- or 6-membered heterocycle having 1 to 3 identical or different heteroatoms from the group consisting of O, S, N, which heterocycle optionally contains a fused-on aromatic 6-membered ring, $R^2$ represents hydrogen, $C_1$–$C_6$-alkoxycarbonyl or $C_1$–$C_6$-alkyl-carbonyl, and n represents 1 or 2.

Particular preference is given to compounds of the formula (I) in which $R^1$ represents hydrogen or represents $C_1$–$C_8$-alkyl which is optionally substituted by $C_1$–$C_3$-alkoxy; $C_1$–$C_3$-alkoxycarbonyl; in each case optionally chlorine- and/or methoxy-substituted phenyl or phenyl-carbonyl; $C_1$–$C_3$-alkylcarbonyl; optionally chlorine-substituted $C_3$–$C_5$-cycloalkylcarbonyl; 5- or 6-membered aromatic heterocyclylcarbonyl having 1 or 2 heteroatoms from the group consisting of N and S; 5- or 6-membered heterocyclylthio having 1 or 2 heteroatoms from the group consisting of N and S, or represents $C_2$–$C_4$-alkenyl, $C_2$–$C_4$-alkinyl, $C_3$–$C_6$-cycloalkyl or represents phenyl which is optionally mono- to trisubstituted by identical or different substituents from the group consisting of chlorine, bromine, fluorine, $C_1$–$C_4$-alkyl, $C_3$–$C_6$-cycloalkyl, $C_1$–$C_3$-alkoxy, $C_1$–$C_2$-haloalkyl, $C_1$–$C_2$-haloalkoxy, hydroxyl, nitro, nitrile, amino, phenoxy, phenyl or di-$C_1$–$C_3$-alkylamino, or represents a 5- or 6-membered aromatic heterocycle having 1 or 2 heteroatoms from the group consisting of N and S and optionally a fused-on phenyl ring, $R^2$ represents hydrogen, $C_1$–$C_3$-alkoxycarbonyl or $C_1$–$C_3$-alkylcarbonyl, and n represents 1 or 2.

Very particular preference is given to compounds of the formula (I) in which $R^1$ represents hydrogen or represents methyl which is optionally substituted by ethoxy, ethoxycarbonyl, phenylcarbonyl, methoxyphenylcarbonyl, chlorophenylcarbonyl, pyrrolylcarbonyl, thienylcarbonyl, chlorocyclopropylcarbonyl, thiazolylthio, thiazinylthio, or represents ethyl, propyl, butyl, octyl, cyclopentyl, benzyl, chlorobenzyl, phenyl, chlorophenyl, methoxyphenyl, methylphenyl, nitrophenyl, dichlorophenyl, trichlorophenyl, fluorophenyl, difluorophenyl, trifluoromethoxyphenyl, trifluoromethylphenyl, thienyl, benzothienyl, bromophenyl, dibromophenyl, nitrilophenyl, dinitrilophenyl, hydroxyphenyl, benzothiazolyl, trifluoromethylthiazolyl, dimethylaminophenyl, phenoxy, phenyl, dimethylphenyl, dimethoxyphenyl, ethylphenyl, propylphenyl, butylphenyl, cyclopropylphenyl, chloromethylphenyl, dichloromethylphenyl, chloromethoxyphenyl, methoxymethylphenyl, methylpropene, allyl, (2-sulfanylthiazolyl)butine, (2-sulfanylthiazinyl)butine, $R^2$ represents hydrogen or methoxycarbonyl and n represents 1 or 2.

The compounds of the formula (I) having the abovementioned general and preferred meanings are novel, and also form part of the subject-matter of the present invention, except for the compounds:

2-(phenylsulfanyl)-5,6-dihydro-4H-1,3-thiazine
CAS No. [73122-32-4]
2-[(3-chlorophenyl)sulfanyl]-5,6-dihydro4H-1,3-thiazine
CAS No. [73122-33-5]
2-[(4-chlorophenyl)sulfanyl]-5,6-dihydro4H-1,3-thiazine
CAS No. [10554-28-6]
2-(methylsulfanyl)-5,6-dihydro-4H-1,3-thiazine
CAS No. [58842-19-6]
2-[(4-methoxyphenyl)sulfanyl]-5,6-dihydro-4H-1,3-thiazine
CAS No. [73122-49-3]
2-[(4-methylphenyl)sulfanyl]-5,6-dihydro4H-1,3-thiazine
CAS No. [73122-44-8]
2-(ethylsulfanyl)-5,6-dihydro-4H-1,3-thiazine,
Beilstein reference No. [4-27-00-01718]
2-[(4-nitrophenyl)sulfanyl]-5,6-dihydro-4H-1,3-thiazine
CAS No. [73122-52-8]
2-[(3,4-dichlorophenyl)sulfanyl]-5,6-dihydro4H-1,3-thiazine,
CAS No. [73122-34-6]
2-[(2-chlorophenyl)sulfanyl]-5,6-dihydro-4H-1,3-thiazine
CAS No. [55545-14-7]
2-(5,6-dihydro4H-1,3-thiazin-2-ylsulfanyl)-1-phenylethanone,
CAS-No. [88636-60-6]
2-{[3-(trifluoromethyl)-1,2,4-thiadiazol-5-yl]sulfanyl}-5,6-di-hydro-4H-1,3-thiazine CAS No. [62655-49-6]
2-[(2,4-dichlorophenyl)sulfanyl]-5,6-dihydro4H-1,3-thiazine
CAS No. [73122-35-7]
2-[(4-bromophenyl)sulfanyl]-5,6-dihydro4H-1,3-thiazine
CAS No. [73122-41-5]
2-[(2,6-dichlorophenyl)sulfanyl]-5,6-dihydro-4H-1,3-thiazine
CAS No. [73122-36-8]

2-[(3,5-dichlorophenyl)sulfanyl]-5,6-dihydro-4H-1,3-thiazine
CAS No. [73122-37-9]
2-[(3-methylphenyl)sulfanyl]-5,6-dihydro4H-1,3-thiazine
CAS No. [73122-45-9]
2-[(2-methylphenyl)sulfanyl]-5,6-dihydro4H-1,3-thiazine
CAS No. [73122-46-0]
4-(5,6-dihydro-4H-1,3-thiazin-2-ylsulfanyl)-N,N-dimethylaniline,
CAS No. [73122-51-7]
2-[(4-fluorophenyl)sulfanyl]-5,6-dihydro4H-1,3-thiazine
CAS No. [73122-42-6]
methyl 2-(methylsulfanyl)-4,5-dihydro-1,3-thiazole4-carboxylate
CAS No. [117389-66-9]
methyl 2-(4-chlorobenzylsulfanyl)4,5-dihydro-1,3-thiazole-4-carboxylate
CAS No. [117389-75-0]
methyl 2-(benzylsulfanyl)4,5-dihydro-1,3-thiazole-4-carboxylate
CAS No. [117389-66-9]
2-[(2-methyl-2-propenyl)sulfanyl]4,5-dihydro-1,3-thiazole
CAS No. [56502-83-1]
2-[benzylsulfanyl]-4,5-dihydro-1,3-thiazole
CAS No. [41834-62-2]
2-[(2-methylpropyl)sulfanyl]-4,5-dihydro-1,3-thiazole
Beilstein reference No. [1099990]
2-[allylsulfanyl]-4,5-dihydro-1,3-thiazole
CAS No. [3571-74-2]
2-[4-nitrophenylsulfanyl]-4,5-dihydro-1,3-thiazole
CAS No. [103482-99-1]
2-[4-methoxyphenylsulfanyl]-4,5-dihydro-1,3-thiazole
CAS No. [13094-98-9]
2-[4-chlorophenylsulfanyl]4,5-dihydro-1,3-thiazole
CAS No. [103482-92-4]
2-[2-chlorophenylsulfanyl]-4,5-dihydro-1,3-thiazole
CAS No. [55545-15-8]
2-[3-chlorophenylsulfanyl]4,5-dihydro-1,3-thiazole
CAS No. [103482-93-5]
2-(4,5-dihydro-1,3-thiazol-2-ylsulfanyl)-1-phenylethanone
CAS No. [17385-78-3]
2-[methylsulfanyl]4,5-dihydro-1,3-thiazole
CAS No. [19975-56-5]
2-{[(4,5-dihydro-1,3-thiazol-2-ylsulfanyl)methyl]sulfanyl}4,5-dihydro-1,3-thiazole CAS No. [89943-80-6]
2-[phenylsulfanyl]-4,5-dihydro-1,3-thiazole
CAS No. [62652-38-4]
2-[(4-tert-butylphenyl)sulfanyl]-5,6-dihydro4H-1,3-thiazine
CAS No. [7312248-2]
2-[(4-chloro-2-methylphenyl)sulfanyl]-5,6-dihydro4H-1,3-thiazine
CAS No. [73122-47-1]
2-[(pentachlorophenyl)sulfanyl]-5,6-dihydro4H-1,3-thiazine
CAS No. [73122-40-4]
2-[(2,4,6-trichlorophenyl)sulfanyl]-5,6-dihydro-4H-1,3-thiazine
CAS No. [73122-39-1]
2-[(2,5-dichlorophenyl)sulfanyl]-5,6-dihydro4H-1,3-thiazine
CAS No. [73122-38-0].

The novel compounds of the formula (I) can be prepared by reacting mercaptans of the formula (II) or salts thereof

in which
R$^1$ is as defined above,
with compounds of the general formula (III)

in which
R$^2$ and n are as defined above and
X represents halogen or a leaving group,
if appropriate in the presence of a diluent and if appropriate in the presence of an acid binder.

Alternatively, the novel compounds of the formula (I) can be prepared by
a) reacting mercaptans of the formula (II) or salts thereof

in which
R$^1$ is as defined above, with isothiocyanates of the general formula (IV)

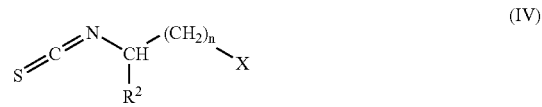

in which
R$^2$ and n are as defined above and
X represents halogen or a leaving group, if appropriate in the presence of a diluent and if appropriate in the presence of an acid binder; or by
b) diazotizing primary amines of the general formula (V)

in which
R$^1$ is as defined above, with a diazotizing agent and reacting the products with compounds of the general formula (VI) or salts thereof

in which
R$^2$ and n are as defined above, if appropriate in the presence of a diluent and if appropriate in the presence of a catalyst, or by c) reacting compounds of the general formula (VII)

R¹—X (VII)

in which
R¹ is as defined above and
X represents halogen or a leaving group, with compounds of the general formula (VI) or salts thereof

(VI)

in which
R² and n are as defined above, if appropriate in the presence of a diluent and if appropriate in the presence of an acid binder.

The salts can be prepared and reacted in situ or employed undiluted. Suitable for use as salts are in particular the alkali and alkaline earth metal salts, preferably the alkali salts and particularly preferably the sodium and potassium salts. The salts are prepared by customary chemical methods.

The starting materials of the general formula (II) to (VII) are commercially available, described in the literature or preparable by simple chemical operations.

The compounds of the general formula (III) and (IV) can, if appropriate, be generated in situ and reacted directly, or they can be employed as pure substance.

Suitable diluents, which are added, if appropriate, are both water and all customary inert organic solvents. These preferably include hydrocarbons, such as toluene, xylene or hexane, chlorinated hydrocarbons, such as chlorobenzene, methylene chloride or chloroform, ketones, such as acetone or butanone, ethers, such as tetrahydrofuran, diethyl ether, methyl tert-butyl ether, dimethoxyethane or dioxane, nitriles, such as acetonitrile, amides, such as N,N-dimethylformamide or N-methylpyrrolidone, sulfoxides, such as dimethyl sulfoxide, sulfones, such as sulfolane, and also esters, such as ethyl acetate or methyl acetate.

In the preparation processes, the reaction temperatures can be varied within a wide temperature range. In general, the processes are carried out between −30° C. and +150° C., preferably between −10° C. and +110° C.

When carrying out the process according to the invention, in general from 1 to 10 mol, preferably from 1 to 5 mol, of the compounds of the general formula (II) or (V) or (VII) are employed per mole of the starting material of the general formula (II) or (IV) or (VI). Work-up is carried out by customary methods.

Suitable for use as acid binders are both organic and inorganic bases. Suitable inorganic bases are carbonates, hydroxides, phosphates and hydrides of the alkali metals, alkaline earth metals and transition metals; preference is given to using the carbonates and hydrides of the alkali metals and alkaline earth metals. Particular preference is given to potassium carbonate, sodium carbonate and caesium carbonate, and also to sodium hydride and potassium hydride. Suitable for use as organic bases are primary, secondary and tertiary amines. Preference is given to tertiary amines, such as trimethylamine, triethylamine, tributylamine, DBU, DBN and pyridine or N,N-dimethylaniline.

The diazotizations can be carried out in the presence of an alkali metal nitrite or an alkyl nitrite. Suitable for use as alkali metal nitrite are all customary alkali metal nitrites; preference is given to using sodium nitrite or potassium nitrite. Suitable for use as alkyl nitrite are all customary alkyl nitrites which, preferably, have 1 to 10 carbon atoms, in particular methyl nitrite, ethyl nitrite, n-propyl nitrite, isopropyl nitrite and isoamyl nitrite. Suitable for use as catalyst are copper, copper salts, palladium or palladium salts. Preference is given to copper turnings, copper(I) iodide, palladium(II) acetate or tetrakis(triphenylphosphine)palladium(0).

The process according to the invention is generally carried out under atmospheric pressure. However, it is also possible to operate at reduced or elevated pressure, namely in the range from 0.1 to 10 bar.

Suitable for use as leaving groups are the esters of sulfonic acids, in particular mesylates, tosylates or triflates.

The novel and known compounds of the formula (I) have potent microbicidal action and can be used for controlling undesirable microorganisms, such as fungi and bacteria, in the protection of materials.

In the protection of materials, the substances according to the invention can be used for protecting industrial materials against attack and destruction by undesirable microorganisms.

In the present context, industrial materials are to be understood as meaning non-live materials which have been prepared for use in industry. For example, industrial materials can be glues, sizes, paper and board, textiles, leather, wood, wooden materials, paints and synthetic articles, cooling lubricants and other materials which can be attacked or destroyed by microorganisms. Parts of production plants, for example cooling-water circuits, which may be impaired by the multiplication of microorganisms may also be understood as industrial materials in the context of the present invention. Industrial materials which are preferably to be protected are glues, sizes, paper and boards, leather, wood, plastics, paints, cooling lubricants and heat transfer liquids.

The compounds (I) to be used according to the invention are particularly suitable for protecting wood, plastics, paints and cooling lubricants against attack by microorganisms.

Examples of microorganisms which are capable of bringing about degradation of, or change in, the industrial materials and which may be mentioned are bacteria, fungi, yeasts, algae and slime organisms. The active compounds according to the invention preferably act against fungi, in particular moulds, wood-discolouring and wood-destroying fungi (Basidiomycetes) and also against slime organisms and algae.

Microorganisms of the following genera may be mentioned by way of example:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*,
*Staphylococcus*, such as *Staphylococcus aureus*.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm-fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Suitable liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as highly disperse silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolysates. Suitable dispersants are: for example lignin-sulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

The active compounds according to the invention, as such or in their formulations, can also be used in a mixture with known fungicides, bactericides, acaricides, nematicides or insecticides, for example to widen the activity spectrum or to prevent the development of resistance. In many cases, synergistic effects are obtained, i.e. the activity of the mixture is greater than the activity of the individual components.

For applications in the protection of materials, the following co-components, for example, are found to be particularly favourable:

imidazoles such as:
clotrimazole, bifonazole, climbazole, econazole, fenapamil, imazalil, isoconazole, ketoconazole, lombazole, miconazole, pefurazoate, prochloraz, triflumizole, thiazolcar, 1-imidazolyl-1-(4'-chlorophenoxy)-3,3-dimethylbutan-2-one, and their metal salts and acid adducts;

triazoles such as:
azaconazole, azocyclotin, bitertanol, bromuconazole, cyproconazole, diclobutrazole, difenoconazole, diniconazole, epoxyconazole, etaconazole, fenbuconazole, fenchlorazole, fenethanil, fluquinconazole, flusilazole, flutriafol, furconazole, hexaconazole, imibenconazole, ipconazole, isozofos, metconazole, myclobutanil, paclobutrazol, penconazole, propioconazole, (±)-cis-1-(4-chlorophenyl)-2-(1H-1,2,4-triazol-1-yl)-cycloheptanol, 2-(1-tert-butyl)-1-(2-chlorophenyl)-3-(1,2,4-triazol-1-yl)-propan-2-ol, tebuconazole, tetraconazole, triadimefon, triadimenol, triapenthenol, triflumizole, triticonazole, uniconazole and their metal salts and acid adducts;

pyridines and pyrimidines such as:
ancymidol, buthiobate, fenarimol, mepanipyrin, nuarimol, pyroxyfur, triamirol;

succinate dehydrogenase inhibitors such as:
benodanil, carboxim, carboxim sulfoxide, cyclafluramid, fenfuram, flutanil, furcarbanil, furmecyclox, mebenil, mepronil, methfuroxam, metsulfovax, pyrocarbolid, oxycarboxin, shirlan, Seedvax;

naphthalene derivatives such as:
terbinafine, naftifine, butenafine, 3-chloro-7-(2-aza-2,7,7-trimethyl-oct-3-en-5-ine);

sulfenamides such as:
dichlofluanid, tolylfluanid, folpet, fluorofolpet, captan, captofol;

benzimidazoles such as:
carbendazim, benomyl, fuberidazole, thiabendazole or their salts;

morpholine derivatives such as:
aldimorph, dimethomorph, dodemorph, falimorph, fenpropidin fenpropimorph, tridemorph, trimorphamid and their arylsulfonate salts such as, for example, p-toluenesulfonic acid and p-dodecylphenylsulfonic acid;

benzothiazoles such as:
2-mercaptobenzothiazole;

benzothiophene dioxides such as:
N-cyclohexyl-benzo[b]thiophene-S,S-dioxide carboxamide;

benzamides such as:
2,6-dichloro-N-(4-trifluoromethylbenzyl)-benzamide, tecloftalam;

boron compounds such as:
boric acid, boric ester, borax;

formaldehyde and formaldehyde-releasing compounds such as:
benzyl alcohol mono-(poly)-hemiformal, n-butanol hemiformal, dazomet, ethylene glycol hemiformal, hexa-hydro-S-triazine, hexamethylenetetramine, N-hydroxymethyl-N'-methylthiourea,
N-methylolchloroacetamide, oxazolidine, paraformaldehyde, taurolin, tetrahydro-1,3-oxazine, N-(2-hydroxypropyl)-amine-methanol;

isothiazolinones such as:
N-methylisothiazolin-3-one, 5-chloro-N-methylisothiazolin-3-one, 4,5-dichloro-N-octylisothiazolin-3-one, 5-chloro-N-octylisothiazolinone, N-octyl-isothiazolin-3-one, 4,5-trimethylene-isothiazolinone, 4,5-benzoisothiazolinone;

aldehydes such as:
cinnamaldehyde, formaldehyde, glutardialdehyde, β-bromocinnamaldehyde;

thiocyanates such as:
thiocyanatomethylthiobenzothiazole, methylenebisthiocyanate;

quaternary ammonium compounds and guanidines such as:
benzalkonium chloride, benzyldimethyltetradecylammonium chloride, benzyldimethyidodecylammonium chloride, dichlorobenzyl-dimethyl-alkylammonium chloride, didecyldimethylammonium chloride, dioctyl-dimethylammonium chloride, N-hexadecyl-trimethyl-ammonium chloride, 1-hexadecyl-pyridinium chloride, iminoctadine tris(albesilate);

iodine derivatives such as:
diiodomethyl p-tolyl sulfone, 3-iodo-2-propinyl alcohol, 4-chlorophenyl-3-iodopropargylformal, 3-bromo-2,3-diiodo-2-propenyl ethylcarbamate, 2,3,3-triiodoallyl alcohol, 3-bromo-2,3-diiodo-2-propenyl alcohol, 3-iodo-2-propinyl n-butyl-carbamate, 3-iodo-2-propinyl n-hexylcarbamate, 3-iodo-2-propinyl-cyclohexylcarbamate, 3-iodo-2-propinyl phenylcarbamate;

phenols such as:
tribromophenol, tetrachlorophenol, 3-methyl-4-chlorophenol, 3,5-dimethyl-4-chlorophenol, phenoxyethanol, dichlorophene, 2-benzyl4-chlorophenol, 5-chloro-2-(2,4-dichlorophenoxy)-phenol, hexachlorophene, p-hydroxybenzoate, o-phenylphenol, m-phenylphenol, p-phenylphenol and their alkali metal salts and alkaline earth metal salts;

microbicides with an activated halogen group such as:
bronopol, bronidox, 2-bromo-2-nitro-1,3-propanediol, 2-bromo-4'-hydroxyacetophenone, 1-bromo-3-chloro4,4,5,5-tetramethyl-2-imidazolidinone, β-bromo-β-nitrostyrene, chloracetamid, chloramin T, 1,3-dibromo4,4,5,5-tetramethyl-2-imidazolidinone, dichloramin T, 3,4-dichloro-(3H)-1,2-dithiol-3-one, 2,2-dibromo-3-nitrilepropionamide, 1,2-dibromo-2,4-dicyanobutane, halane, halazone, mucochloric acid, phenyl (2-chlorocyano-vinyl)sulfone, phenyl (1,2-dichloro-2-cyanovinyl) sulfone, trichloroisocyanuric acid;

pyridines such as:
1-hydroxy-2-pyridinethione (and their Na, Fe, Mn, Zn salts), tetrachloro4-methylsulfonylpyridine, pyrimethanol, mepanipyrim, dipyrithion, 1-hydroxy-4-methyl-6-(2,4,4-trimethylpentyl)-2(1H)-pyridine;

methoxyacrylates or similar such as:
azoxystrobin,
methyl (E)-methoximino[alpha-(o-tolyloxy)-o-tolyl]acetate,
(E)-2-methoxyimino-N-methyl-2-(2-phenoxyphenyl)acetamide,
(E)-2-{2-[6-(2-cyanophenoxy)pyrimidin-4-yloxy]phenyl}3-methoxyacrylate,
O-methyl 2-[([3-methoximino-2-butyl)imino]oxy)o-tolyl]-2-methoximino-acet-imidate,
2-[[[[1-(2,5-dimethylphenyl)ethylidene]amino]oxy]methyl]-alpha-(methoximino)-N-methylbenzeneacetamide,
alpha-(methoxyimino)-N-methyl-2-[[[[1-[3-(trifluoromethyl)phenyl]ethylidene]amino]oxy]methyl]-benzeneacetamide, trifloxystrobin,
alpha-(methoxymethylene)-2-[[[[1-[3-(trifluoromethyl)phenyl]ethylidene]amino]oxy]methyl]-benzeneacetic acid methyl ester,
2-[[[5-chloro-3-(trifluoromethyl)-2-pyridinyl]oxy]methyl]-alpha-(methoxyimino)-N-methylbenzeneacetamide,
2-[[[cyclopropyl[(4-ethoxyphenyl)imino]methyl]thio]methyl]-alpha-(methoxyimino)-benzeneacetic acid methyl ester,
alpha-(methoxyimino)-N-methyl-2-(4-methyl-5-phenyl-2,7-dioxa-3,6-diazaocta-3,5-dien-1-yl)-benzeneacetamide,
alpha-(methoxymethylene)-2-(4-methyl-5-phenyl-2,7-dioxa-3,6-diazaocta-3,5-dien-1-yl)-benzeneacetic acid methyl ester,
alpha-(methoxyimino)-N-methyl-2-[[[1-[3-(trifluoromethyl)phenyl]ethoxy]imino]-methyl]-benzeneacetamide,
2-[[(3,5-dichloro-2-pyridinyl)oxy]methyl]-alpha-(methoxyimino)-N-methyl-benzeneacetamide,
2-[4,5-dimethyl-9-(4-morpholinyl)-2,7-dioxa-3,6-diazanona-3,5-dien-1-yl]-alpha-(methoxymethylene)-benzeneacetic acid methyl ester,
kresoxim-methyl;

metal soaps such as:
tin naphthenate, copper napthenate, zinc napthenate, tin octoate, copper octoate, zinc octoate, tin 2-ethylhexanoate, copper 2-ethylhexanoate, zinc 2-ethylhexanoate, tin oleate, copper oleate, zinc oleate, tin phosphate, copper phosphate, zinc phosphate, tin benzoate, copper benzoate, zinc benzoate;

metal salts such as:
copper hydroxycarbonate, sodium dichromate, potassium dichromate, potassium chromate, copper sulfate, copper chloride, copper borate, zinc fluorosilicate, copper fluorosilicate;

oxides such as:
tributyltin oxide, $Cu_2O$, $CuO$, $ZnO$;

dithiocarbamates such as:
cufraneb, ferban, potassium N-hydroxymethyl-N'-methyldithiocarbamate, sodium dimethyldithiocarbamate, potassium dimethyldithiocarbamate, macozeb, maneb, metam, metiram, thiram, zineb, ziram;

nitriles such as:
2,4,5,6-tetrachloroisophthalonitrile, disodium cyano-dithio-imidocarbamate;

quinolines such as:
8-hydroxyquinoline and its copper salts;

other fungicides and bactericides such as:
5-hydroxy-2(5H)-furanone, 4,5-benzodithiazolinone, 4,5-trimethylenedithiazolinone, N-(2-p-chlorobenzoylethyl)-hexaminium chloride, 2-oxo-2-(4-hydroxy-phenyl)-acetohydroxamic acid chloride, tris-N-(cyclohexyldiazeniumdioxy)-aluminium, N-(cyclohexyldiazeniumdioxy)-tributyltin or its potassium salts, bis-N-(cyclohexyldiazeniumdioxy)-copper, iprovalicarb, fenhexamid, spiroxamine, carpropamid, diflumetorin, quinoxyfen, famoxadone, polyoxorim, acibenzolar S-methyl, furametpyr, thifluzamide, methalaxyl-M, Ag—, Zn— or Cu-containing zeolites alone or incorporated into polymeric materials.

Very especially preferred are mixtures of compounds of the formula (I) to be used according to the invention with one or more of the following active compounds:

azaconazole, bromuconazole, cyproconazole, dichlobutrazol, diniconazole, hexaconazole, metaconazole, penconazole, propiconazole, tebuconazole, dichlofluanid, tolylfluanid, fluorfolpet, methfuroxam, carboxin, benzo[b]thiophene S,S-dioxide N-cyclohexylcarboxamide, fenpiclonil, 4-(2,2-difluoro-1,3-benzodioxol-4-yl)-1H-pyrrole-3-carbonitrile, butenafine, imazalil, N-methylisothiazolin-3-one, 5-chloro-N-methylisothiazolin-3-one, N-octylisothiazolin-3-one, dichloro-N-octylisothiazolinone, mercaptobenthiazole, thiocyanatomethylthiobenzothiazole, benzoisothiazolinone, N-(2-hydroxypropyl)-amino-methanol, benzyl alcohol (hemi)-formal, N-methylolchloroacetamide, N-(2-hydroxypropyl)-amine-methanol, glutaraldehyde, omadine, dimethyl dicarbonate, 2-bromo-2-nitro-1,3-propanediol and/or 3-iodo-2-propinyl n-butylcarbamate.

Apart from with the abovementioned fungicides and bactericides, mixtures with a good efficacy are, moreover, also prepared, for example with one or more of the following active compounds:

insecticides/acaricides/nematicides:

abamectin, acephate, acetamiprid, acrinathrin, alanycarb, aldicarb, aldoxycarb, aldrin, allethrin, alpha-cypermethrin, amitraz, avermectin, AZ 60541, azadirachtin, azinphos A, azinphos M, azocyclotin,

*Bacillus thuringiensis*, barthrin, 4-bromo-2(4-chlorophenyl)-1-(ethoxymethyl)-5-(trifluoromethyl)-1H-pyrrole-3-carbonitrile, bendiocarb, benfuracarb, bensultap, betacyfluthrin, bifenthrin, bioresmethrin, bioallethrin, bromophos A, bromophos M, bufencarb, buprofezin, butathiophos, butocarboxin, butoxycarboxim, cadusafos, carbaryl, carbofuran, carbophenothion, carbosulfan, cartap, quinomethionate, cloethocarb, chlordane, chlorethoxyfos, chlorfenapyr, chlorfenvinphos, chlorfluazuron, chlormephos, N-[(6-chloro-3-pyridinyl)-methyl]-N'-cyano-N-methyl-ethaneimidamide, chlorpicrin, chlorpyrifos A, chlorpyrifos M, cis-resmethrin, clocythrin, cypophenothrin, clofentezin, coumaphos, cyanophos, cycloprothrin, cyfluthrin, cyhalothrin, cyhexatin, cypermethrin, cyromazin, decamethrin, deltamethrin, demeton M, demeton S, demeton-S-methyl, diafenthiuron, dialiphos, diazinon, 1,2-dibenzoyl-1(1,1-dimethyl)-hydrazine, DNOC, dichlofenthion, dichlorvos, dicliphos, dicrotophos, difethialone, diflubenzuron, dimethoate, dimethyl-(phenyl)-silyl-methyl 3-phenoxybenzyl ether, dimethyl-(4-ethoxyphenyl)-silylmethyl-3-phenoxybenzyl ether, dimethylvinphos, dioxathion, disulfoton, eflusilanate, emamectin, empenthrin, endosulfan, EPN, esfenvalerate, ethiofencarb, ethion, ethofenprox, etrimphos, etoxazole, etobenzanid, fenamiphos, fenazaquin, fenbutatin oxide, fenfluthrin, fenitrothion, fenobucarb, fenothiocarb, fenoxycarb, fenpropathrin, fenpyrad, fenpyroximat, fensulfothion, fenthion, fenvalerate, fipronil, fluazuron, flucycloxuron, flucythrinate, flufenoxuron, flupyrazofos, flufenzine, flumethrin, flufenprox, fluvalinate, fonophos, formethanate, formothion, fosmethilan, fosthiazate, fubfenprox, furathiocarb, halofenocid, HCH, heptenophos, hexaflumuron, hexythiazox, hydramethylnon, hydroprene, imidacloprid, imiprothrin, indoxycarb, iodfenfos, iprinomectin, iprobenfos, isazophos, isoamidophos, isofenphos, isoprocarb, isoprothiolane, isoxathion, ivermectin, lama-cyhalothrin, lufenuron, kadedrin lambda-cyhalothrin, lufenuron, malathion, mecarbam, mervinphos, mesulfenphos, metaldehyde, methacrifos, methamidophos, methidathion, methiocarb, methomyl, metalcarb, milbemectin, monocrotophos, moxiectin, naled, NC 184, NI 125, nicotine, nitenpyram, omethoate, oxamyl, oxydemethon M, oxydeprofos, parathion A, parathion M, penfluron, permethrin, 2-(4-phenoxyphenoxy)-ethyl ethylcarbamate, phenthoate, phorate, phosalon, phosmet, phosphamidon, phoxim, pirimicarb, pirimiphos M, pirimiphos A, prallethrin, profenophos, promecarb, propaphos, propoxur, prothiophos, prothoate, pymetrozin, pyrachlophos, pyridaphenthion, pyresmethrin, pyrethrum, pyridaben, pyrimidifen, pyriproxifen, pyrithiobac-sodium, quinalphos, resmethrin, RH-7988, rotenone, salithion, sebufos, silafluofen, spinosad, sulfotep, sulprofos, tau-fluvalinate, taroils, tebufenozide, tebufenpyrad, tebupirimphos, teflubenzuron, tefluthrin, temephos, terbam, terbufos, tetrachlorvinphos, tetramethrin, tetramethacarb, thiacloprid, thiafenox, thiamethoxam, thiapronil, thiodicarb, thiofanox, thiazophos, thiocyclam, thiomethon, thionazin, thuringiensin, tralomethrin, transfluthrin, triarathen, triazophos, triazamate, triazuron, trichlorfon, triflumuron, trimethacarb, vamidothion, XMC, xylylcarb, zetamethrin;

molluscicides fentin acetate, metaldehyde, methiocarb, niclosamide;

herbicides and algicides acetochlor, acifluorfen, aclonifen, acrolein, alachlor, alloxydim, ametryn, amidosulfuron, amitrole, ammonium sulfamate, anilofos, asulam, atrazine, azafenidin, aziptrotryne, azimsulfuron, benazolin, benfluralin, benfuresate, bensulfuron, bensulfide, bentazone, benzofencap, benzthiazuron, bifenox, bispyribac, borax, bromacil, bromobutide, bromofenoxim, bromoxynil, butachlor, butamifos, butralin, butylate, bialaphos, benzoyl-prop, bromobutide, butroxydim, carbetamide, carfentrazone-ethyl, carfenstrole, chlomethoxyfen, chloramben, chlorbromuron, chlorflurenol, chloridazon, chlorimuron, chlornitrofen, chloroacetic acid, chloransulam-methyl, cinidon-ethyl, chlorotoluron, chloroxuron, chlorpropham, chlorsulfuron, chlorthal, chlorthiamid, cinmethylin, cinofulsuron, clefoxydim, clethodim, clomazone, chlomeprop, clopyralid, cyanamide, cyanazine, cycloate, cycloxydim, chloroxynil, clodinafop-propargyl, cumyluron, CGA 248757, clometoxyfen, cyhalofop, cyhalofop-butyl, clopyrasuluron, cyclosulfamuron, diclosulam, dichlorprop, dichlorprop-P, diclofop, diethatyl, difenoxuron, difenzoquat, diflufenican, diflufenzopyr, dimefuron, dimepiperate, dimethachlor, dimethipin, dinitramine, dinoseb, dinoseb acetate, dinoterb, diphenamid, dipropetryn, diquat, dithiopyr, diduron, DNOC, DSMA, 2,4-D, daimuron, dalapon, dazomet, 2,4-DB, desmedipham, desmetryn, dicamba, dichlobenil, dimethamid, dithiopyr, dimethametryn, eglinazine, endothal, EPTC, esprocarb, ethalfluralin, ethidimuron, ethofumesate, ethobenzanid, ethoxyfen, ET 751, ethametsulfuron, ethoxysulfuron, fenoxaprop, fenoxaprop-P, fenuron, flamprop, flamprop-M, flazasulfuron, fluazifop, fluazifop-P, fuenachlor, fluchloralin, flufenacet, flumeturon, fluorocglycofen, fluoronitrofen, flupropanate, flurenol, fluridone, flurochloridone, fluroxypyr, fomesafen, fosamine, flamprop-isopropyl, flamprop-isopropyl-L, flumiclorac-pentyl, flumipropyn, flumioxzim, flurtamone, flumioxzim, flupyrsulfuron-methyl, glyphosate, glufosinate-ammonium haloxyfop, hexazinone, imazamethabenz, isoproturon, isoxaben, isoxapyrifop, imazapyr, imazaquin, imazethapyr, ioxynil, isopropalin, imazosulfuron, imazomox, isoxaflutole, imazapic,

KUH 911, KUH 920 lactofen, lenacil, linuron, LS830556,

MCPA, MCPA-thioethyl, MCPB, mecoprop, mecoprop-P, mefenacet, mefluidide, metam, metamitron, metazachlor, methabenzthiazuron, methazole, methoroptryne, methyldymron, methyl isothiocyanate, metobromuron, metoxuron, metribuzin, metsulfuron, molinate, monalide, monolinuron, MSMA, metolachlor, metosulam, metobenzuron, naproanilide, napropamide, naptalam, neburon, nicosulfuron, norflurazon, sodium chlorate, oxadiazon, oxyfluorfen, oxysulfuron, orbencarb, oryzalin, oxadiargyl, propyzamide, prosulfocarb, pyrazolate, pyrazolsulfuron, pyrazoxyfen, pyribenzoxim, pyributicarb, pyridate, paraquat, pebulate, pendimethalin, pentachlorophenol, pentoxazone, pentanochlor, petroleum oils, phenmedipham, picloram, piperophos, pretilachlor, primisulfuron, prodiamine, prometryn, propachlor, propanil, propaquizafob, propazine, propham, propisochlor, pyriminobac-methyl, pelargonic acid, pyrithiobac, quinmerac, quinocloamine, quizalofop, quizalofop-P, quinchlorac, rimsulfuron sethoxydim, sifuron, simazine, simetryn, sulfosulfuron, sulfometuron, sulfentrazone, sulcotrione, sulfosate, tar oils, TCA, tebutam, tebuthiuron, terbacil, terbumeton, terbuthylazine, terbutryn, thiazafluoron, thifensulfuron, thiobencarb, thiocarbazil, tralkoxydim, triallate, triasulfuron, tribenuron, triclopyr, tridiphane, trietazine, trifluralin, tycor, thdiazimin, thiazopyr, triflusulfuron, vernolate.

The active compounds can be applied as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading-on and the like.

The compositions used for protecting industrial materials generally comprise the active compounds in an amount of from 1 to 95%, preferably from 10 to 75%.

The use concentrations of the active compounds according to the invention depend on the type and the occurrence of the microorganisms to be controlled, and on the composition of the material to be protected. The optimal rate can be determined by test series. In general, the use concentrations are in the range from 0.001 to 5% by weight, preferably from 0.05 to 1.0% by weight, based on the material to be protected.

The invention is further described in the following illustrative examples in which all parts and percentages are by weight unless otherwise indicated.

EXAMPLES

Preparation Examples

Example 1

3.2 g (0.02 mol) of methyl 1,3-thiazolidine-2-thione-4-carboxylate are initially charged in acetonitrile, and 2.27 g (0.022 mol) of triethylamine and subsequently 3.43 g (0.022 mol) of ethyl iodide are added. The reaction mixture is stirred at room temperature for 4 days, water is added and the mixture is extracted. The crude product obtained after drying of the organic phase and concentration is chromatographed, giving the thiazole of the general formula (I) where $R^1$=ethyl, $R^2$ =$CO_2$Me and n=1 as a pale yellow oil.

Yield: 2.0 g (49% of theory), $n_D^{26}$=1.5485

Example 2

$K_2CO_3$ (2.07 g, 0.015 mol) is initially charged in acetonitrile, and 1,3-thiazolidine-2-thione (1.19 g, 0.01 mol) in acetonitrile is added. 2-Chloro-1-(1H-pyrrol-2-yl)ethanone (1.43 g, 0.01 mol) is dissolved in acetonitrile and metered in. The reaction mixture is stirred at room temperature for 16 h and heated at 40° C. for another 8 h. The solid is filtered off, the reaction mixture is concentrated and the residue is taken up in $CH_2Cl_2$ and washed with water. Drying and concentration give the thiazine of the general formula (I) where

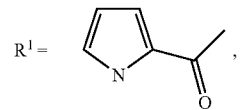

$R^2$=H and n=1.

Yield: 1.7 g (65% of theory) m.p.=103–105° C.

Example 3

2-Mercaptothiophene (0.56 g, 5.75 mmol) and triethylamine (0.58 g, 5.75 mmol) are initially charged in acetone (50 ml), and the mixture is stirred at room temperature for about 10 minutes. 1.0 g (5.75 mmol) of 1-bromo-2-isothiocyanatoethane is added. The reaction mixture is stirred under reflux for 4 h, water is added and the mixture is extracted. The organic phase is dried and concentrated, giving the thiazole of the general formula (I) where

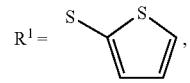

$R^2$=H and n=1 as an oil.

Yield: 0.69 g (60% of theory), $\delta(CDCl_3)$=3.30 (m, 2H), 4.30 (m, 2H), 7.05–7.60 (m, 3H)

Example 4

1.85 g (0.015 mol) of p-methoxyaniline are suspended in water (25 ml), acidified using conc. hydrochloric acid (3.8 ml) and cooled to 0° C. A solution of 1.10 g (0.016 mol) of sodium nitrite in water (about 8 ml) is added dropwise. The solution is stirred at 0° C. for 1 h and then adjusted to about pH 4.5–5 using sodium acetate. At 0° C., this solution is added dropwise to a solution of 2.43 g (0.015 mol) of methyl 1,3-thiazolidine-2-thione-4-carboxylate in acetone (75 ml) and water (6 ml) containing 0.6 g of sodium hydroxide and 4.4 g of sodium acetate. The reaction mixture is stirred at this temperature for 1 h, water is added and the mixture is extracted. The residue that remains after drying and concentration is chromatographed, giving the thiazole of the general formula (I) where R1=p-MeOC$_6$H$_4$, R2=CO$_2$Me and n=1 as an oil.

Yield: 1.13 g (27% of theory); $n_D^{26}$=1.5990

Example 5

34.42 g (0.2 mol) of 2-chloro-5,6-dihydro-4H-1,3-thiazine hydrochloride are dissolved in water and adjusted to about pH 10 using K$_2$CO$_3$. The solution is stirred for 30 minutes and extracted with ethyl acetate. The organic phase is dried and evaporated to dryness under reduced pressure. The oil is dissolved in DMF. Under an atmosphere of nitrogen, this solution is added dropwise to a suspension of 21.95 g (0.191 mol) of 2-mercapto-thiophene and 8.39 g (0.21 mol) of sodium hydride in DMF which had been stirred at room temperature for 30 minutes, and the mixture is stirred at 100° C. for 4.5 hours and at room temperature for 16 h. Water is added, and the mixture is extracted with ethyl acetate. The organic phase is dried and concentrated. The residue is chromatographed, giving the thiazine of the general formula (I) where

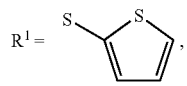

R$^2$=H and n=2.

Yield: 0.5 g (20% of theory), $n_D^{20}$=1.5660

Example 6

2.5 g (0.021 mol) of 1,3-thiazine-2-thione and 3.17 g (0.023 mol) of K$_2$CO$_3$ are together initially charged in acetonitrile. 0.032 mol of octyl bromide is added dropwise to the suspension. The reaction mixture is stirred at room temperature for 16 h, water is added and the mixture is extracted with ethyl acetate. The organic phase is dried and concentrated. The residue is separated by column chromatography, giving the thiazine of the general formula (I) where R1=n-octyl, R2=H and n=2.

Yield: 1.08 g (21% of theory), $n_D^{20}$=1.5465

The substances of the general formula (I) listed in Table 1 are prepared analogously to Examples 1 to 6 and/or in accordance with the general statements in the description of the experiments.

TABLE 1

| Example | R$^1$ | R$^2$ | n | Physical data |
|---|---|---|---|---|
| 7 | propyl | CO$_2$Me | 1 | $n_D^{26}$=1.5445 |
| 8 | iso-propyl | CO$_2$Me | 1 | $n_D^{26}$=1.5440 |
| 9 | cyclo-pentyl | CO$_2$Me | 1 | $n_D^{26}$=1.5755 |
| 10 | EtO—CO—CH$_2$ | CO$_2$Me | 1 | $n_D^{26}$=1.5350 |
| 11 | C$_6$H$_5$—CO—CH$_2$ | CO$_2$Me | 1 | $n_D^{26}$=1.6210 |
| 12 | (cyclopropyl-C(O)-C(CH$_3$)(Cl)-) | H | 1 | δ(CDCl$_3$)=1.45(m, 2H), 1.75(m, 2H), 3.40(m, 2H), 4.15(m, 2H), 4.50(s, 2H) |
| 13 | 3,4-Cl$_2$C$_6$H$_3$ | H | 1 | δ(CDCl$_3$)= 3.38(m, 2H), 4.25(m, 2H), 7.4–7.7(m, 3H) |
| 14 | 4-CF$_3$O—C$_6$H$_4$ | H | 1 | δ(CDCl$_3$)=3.35(m, 2H), 4.30(m, 2H), 7.20–7.67(m, 4H) |
| 15 | 4-CH$_3$C$_6$H$_4$ | CO$_2$Me | 1 | δ(CDCl$_3$)=2.35(s, 3H), 3.50(m, 2H), 3.80(s, 3H), 5.15(m, 1H), 7.20–7.55(m, 4H) |
| 16 | C$_6$H$_5$ | CO$_2$Me | 1 | $n_D^{26}$=1.6140 |
| 17 | 4-BrC$_6$H$_4$ | CO$_2$Me | 1 | m.p.=99.5° C. |
| 18 | 3-ClC$_6$H$_4$ | CO$_2$Me | 1 | δ(CDCl$_3$)=3.58(m, 2H), 3.80(s, 3H), 5.15(m, 1H), 7.15–7.75(m, 4H) |
| 19 | (thiazoline-S-CH$_2$-C≡C-CH$_2$-) | H | 1 | m.p.=72° C. |
| 20 | EtOCH$_2$ | H | 1 | δ(CDCl$_3$)=1.20(t, 3H), 3.30(m, 2H), 3.65(m, 3H), 4.15(m, 2H), 5.18(s, 2H) |

TABLE 1-continued

| Example | R¹ | R² | n | Physical data |
|---|---|---|---|---|
| 21 | H₂C-C(=O)-(2-thienyl) | H | 1 | δ(CDCl₃)=3.45(m, 2H), 4.20(m, 2H), 4.55(s, 2H), 7.15–7.85(m, 3H) |
| 22 | benzyl | H | 2 | δ(CDCl₃)=2.20(m, 2H), 2.95(m, 2H), 3.45(m, 2H), 5.38(s, 2H), 7.2–7.45(m, 5H) |
| 23 | EtOCH₂ | H | 2 | m.p.=49° C. |
| 24 | butyl | H | 2 | $n_D^{23}$=1.6028 |
| 25 | 3-MeOC₆H₄ | H | 2 | $n_D^{23}$=1.5795 |
| 26 | 2-MeOC₆H₄ | H | 2 | m.p.=165° C. |
| 27 | H₂C-C(=O)-(2-thienyl) | H | 2 | $n_D^{23}$=1.5485 |
| 28 | CH₃-C≡C-CH₂-S-(4,5-dihydro-1,3-thiazin-2-yl) | H | 2 | m.p.=66–67° C. |
| 29 | H₂C-C(=O)-(2-pyrrolyl) | H | 2 | $n_D^{23}$=1.5680 |
| 30 | 4-MeO—C₆H₄—CO—CH₂ | H | 2 | m.p.=102–103° C. |
| 31 | allyl | H | 2 | δ(CDCl₃)=2.30(m, 2H), 3.00(m, 2H), 3.45(m, 2H), 4.75(m, 2H), 5.28(m, 2H), 5.85(m, 1H) |
| 32 | CH₃-CH₂-S-(4,5-dihydro-1,3-thiazin-2-yl) | H | 2 | m.p.=65–66° C. |
| 33 | 4-CF₃O—C₆H₄ | H | 2 | δ(CDCl₃)=1.85(m, 2H), 3.05(m, 2H), 3.75(m, 3H), 7.15–7.60(m, 4H) |
| 34 | 2-methylbenzothiazole | H | 2 | m.p.=114.5° C. |
| 35 | 3-MeO—C₆H₄ | H | 2 | $R_f$=0.44(toluene 5, ethyl acetate 1) |
| 36 | 2-MeO—C₆H₄ | H | 2 | $R_f$=0.30(toluene 5, ethyl acetate 1) |
| 37 | 2,6-Me₂—C₆H₃ | H | 2 | m.p.=205° C. |
| 38 | 4-HO—C₆H₄ | H | 2 | m.p.=210° C. |
| 39 | 3-FC₆H₄ | H | 2 | $R_f$=0.32(toluene 10, ethyl acetate 1) |
| 40 | 4-CF₃—C₆H₄ | H | 2 | m.p.=125° C. |
| 41 | 3-HO—C₆H₄ | H | 2 | m.p.=197° C. |
| 42 | 3,4-(MeO)₂—C₆H₃ | H | 2 | $R_f$=0.24(toluene 10, ethyl acetate 1) |
| 43 | 3-CF₃—C₆H₄ | H | 2 | $R_f$=0.48(toluene 1, ethyl acetate 1) |

TABLE 1-continued

| Example | $R^1$ | $R^2$ | n | Physical data |
|---|---|---|---|---|
| 44 | 4-$C_2H_5$—$C_6H_4$ | H | 2 | $R_f$=0.32(toluene 10, ethyl acetate 1) |
| 45 | 4-($C_6H_5O$)—$C_6H_4$ | H | 2 | $R_f$=0.43(toluene 10, ethyl acetate 1) |
| 46 | 3-($C_6H_5O$)—$C_6H_4$ | H | 2 | $R_f$=0.41(toluene 10, ethyl acetate 1) |
| 47 | 4-($CH_6H_5$)—$C_6H_4$ | H | 2 | $R_f$=0.46(toluene 10, ethyl acetate 1) |
| 48 | 3-($C_6H_5$)—$C_6H_4$ | H | 2 | $R_f$=0.44(toluene 10, ethyl acetate 1) |
| 49 | 4-(cyclo-propyl)-$C_6H_4$ | H | 2 | $R_f$=0.07(toluene |

Use Example A

To demonstrate the activity against bacteria, the minimum inhibitory concentrations (MIC) of the agents according to the invention are determined:

The active compounds according to the invention are in each case added, in concentrations of from 0.1 mg/ml to 5000 mg/ml, to a chemically defined nutrient agar. After the agar has solidified, it is contaminated with pure cultures of the test organisms listed in Table 2. The MIC is determined after 3 days of incubation at 28° C. and 60 to 70% relative atmospheric humidity. MIC is the lowest concentration of active compound at which the microbial species used does not grow at all; it is stated in Table 2.

TABLE 2

Minimum inhibitory concentration (ppm) of the compounds of the formula (I) according to the invention

| Example No./CAS No. | *Bacillus subtilis* |
|---|---|
| 22 | 100 |
| 73122-32-4 | <100 |
| 27 | <100 |
| 73122-35-7 | <40 |
| 73122-37-9 | 100 |
| 8 | <200 |
| 3571-74-2 | 200 |

Use Example B

To demonstrate the activity against fungi, the minimum inhibitory concentrations (MIC) of agents according to the invention are determined:

The active compounds according to the invention are in each case added, in concentrations of from 0.1 mg/l to 5000 mg/l, to an agar which is prepared using malt extract. After the agar has solidified, it is contaminated with pure cultures of the test organisms listed in Table 3. The MIC is determined after 2 weeks of incubation at 28° C. and 60 to 70% relative atmospheric humidity.

MIC is the lowest concentration of active compound at which the microbial species used does not grow at all; it is stated in Table 3.

Table 3 Minimum inhibitory concentrations (ppm) of compounds of the formula (I) according to the invention

TABLE 3

| Example No./CAS No. | *Penicillium brevicaule* | *Chaetomium globosum* | *Aspergillus niger* |
|---|---|---|---|
| 73122-32-4 | <200 | <200 | <300 |
| 10554-28-6 | <200 | <200 | <400 |
| 73122-49-3 | <300 | <400 | <400 |
| 73122-33-5 | <200 | <200 | 200 |
| 73122-44-8 | <100 | <200 | <250 |
| 73122-52-8 | <200 | <100 | <150 |
| 73122-34-6 | <100 | <100 | 400 |
| 55545-14-7 | <200 | <200 | <200 |
| 26 | 100 | 200 | |
| 5 | <100 | <100 | <200 |
| 32 | <200 | <200 | |
| 73122-41-5 | <200 | <200 | <300 |
| 73122-45-9 | <100 | <100 | <200 |
| 103482-99-1 | <200 | <200 | |
| 103482-92-4 | 200 | <200 | |
| 103482-93-5 | 200 | <200 | |
| 18 | | 200 | |
| 754-1-1 | 200 | 100 | |
| 822-1-1 | <200 | <300 | |
| 73122-51-7 | 100 | <100 | 200 |
| 73122-48-2 | <100 | <100 | 100 |
| 73122-46-0 | 100 | <200 | 200 |
| 73122-42-6 | <50 | <100 | 100 |
| 36 | 100 | 100 | 100 |
| 39 | <100 | <100 | 100 |
| 44 | <100 | <100 | 100 |
| 37 | 400 | <200 | |
| 40 | <100 | <100 | <250 |
| 41 | 100 | 200 | |
| 42 | <200 | 100 | 500 |
| 45 | 100 | <100 | |
| 48 | 200 | <100 | |
| 49 | <100 | <100 | 100 |

Use Example C

To test dispersion coatings for resistance to mould, the following procedure is adopted:

The paint to be tested is applied to both sides of a suitable base. To obtain results which are close to practice, some of the test specimens are leached out with running water (24 h, 20° C.) before the test for mould resistance; others are treated with a current of warm fresh air (7 days, 40° C.).

The samples prepared in this way are then placed on an agar nutrient medium, and both samples and nutrient medium are contaminated with fungal spores. After 2–3 weeks storage (29±1° C., 80–90% rel. atmospheric humidity), the samples are compared.

The coating is considered to be permanently mould-resistant if the sample remains free from fungus or at most a slightly border infestation can be detected.

For the contamination, fungal spores of the following mould fungi are used, which are known as paint destroyers or are frequently encountered on coatings:

*Alternaria tenius*
*Aspergillus flavus*
*Aspergillus niger*
*Aspergillus ustus*
*Cindosporum herbarum*
*Paecilomyces variotii*
*Penicillium citrium*
*Aureobasidium pullulans*
*Stachybotrys chartarum*

Coatings according to recipe A are mould-resistant (even after leaching out and wind tunnel exposure) if they contain, for example, 1.5% (based on solids) of the compound of Example 25.

Recipe A: Exterior dispersion paint based on Acroal 290 D (styrene acrylate)

| Tradename | Parts by weight | Chemical name |
| --- | --- | --- |
| Bayer Titan RKB2 | 40 | Titanium dioxide |
| Talkum V58 new | 10 | Magnesium silicate, containing water |
| Durcal 5 | 45 | Calcite CaCO$_3$ |
| Walsroder MC 3000 S 2% | 30 | Methylcellulose |
| H$_2$O | 6.5 | Distilled water |
| Calgon N 10% | 3 | Polyphosphate |
| Pigmentverteiler A 10% | 1 | Polyacrylic acid salt |
| Agitan 281, 1:1 inTexanol | 1 | |
| White spirit | 5 | Mixture of aliph. hydrocarbons |
| Butyl glycol acetate | 1.5 | Butyl glycol acetate |
| Acronal 290 D (binder) | 71 | Polyacrylic acid ester |
| Total | 219 | |

Solids content 135.5 = 61.6%.

Although the present invention has been described in detail with reference to certain preferred versions thereof, other variations are possible. Therefore, the spirit and scope of the appended claims should not be limited to the description of the versions contained therein.

What is claimed is:

1. A method for protecting an industrial material selected from glues, sizes, paper and board, textiles, leather, wood, wooden materials, paints, synthetic articles, cooling lubricants and combinations thereof, against attack and destruction by a microorganism selected from bacteria, fungi, yeast, algae, and slime organisms, comprising treating the industrial material with a compound at the formula (I)

wherein
R$^1$ represents hydrogen or in each case optionally substituted alkyl, alkenyl, alkinyl, cycloalkyl, aryl or heterocyclyl,
R$^2$ represents hydrogen, alkoxycarbonyl or alkylcarbonyl and n represents 2.

2. The method according to claim 1, wherein in formula (I)
R$^1$ represents hydrogen or represents C$_1$–C$_{12}$-alkyl which is optionally mono- or polysubstituted by identical or different substituents from the group consisting of C$_1$–C$_6$-alkoxy; C$_1$–C$_6$-alkaxycarbonyl; in each case optionally halogen- and/or C$_1$–C$_6$-alkoxy-substituted phenyl or phenyl-carbonyl; C$_1$–C$_6$-alkylcarbonyl; optionally halogen-substituted C$_3$–C$_8$-cycloalkylcarbonyl; 5- or 6-membered heterocyclylcarbonyl having 1 to 3 heteroatoms from the group consisting of N, O and S; 5- or 6-membered heterocyclylthio having 1 to 3 heteroatoms from the group consisting of N, O and S; or represents C$_2$–C$_6$-alkenyl, C$_2$–C$_6$-alkinyl, C$_3$–C$_8$-cycloalkyl or represents phenyl which is optionally mono- or polysubstituted by identical or different substituents from the group consisting of halogen, C$_1$–C$_6$-alkyl, C$_3$–C$_8$-cycloalkyl, C$_1$–C$_6$-haloalkyl, C$_1$–C$_6$-haloalkoxy, C$_1$–C$_6$-alkoxy, nitro, nitrile, hydroxyl, amino, phenoxy, phenyl and di-C$_1$–C$_6$-alkylamino, or represents a 5- or 6-membered heterocycle having 1 to 3 identical or different heteroatoms from the group consisting of O, S, N, which heterocycle optionally contains a fused-on aromatic 6-membered ring,
R$^2$ represents hydrogen, C$_1$–C$_6$-alkoxycarbonyl or C$_1$–C$_6$-alkylcarbonyl, and
n represents 2.

3. The method according to claim 1, wherein the industrial material is wood or timber and the wood or timber are protected against attack by wood-destroying and/or wood-discolouring fungi.

4. A compound of the formula (I):

wherein
R$^1$ represents hydrogen or represents phenyl which is optionally mono- or polysubstituted by identical or different substituents from the group consisting of halogen, $C_1$–$C_6$-alkyl, $C_3$–$C_8$-cycloalkyl, $C_1$–$C_6$-haloalkyl, $C_1$–$C_6$-haloalkoxy, $C_1$–$C_6$-alkoxy, nitro, nitrile, hydroxyl, amino, phenoxy, phenyl and di-$C_1$–$C_6$-alkylamino, $R^2$ represents hydrogen, $C_1$–$C_6$-alkoxycarbonyl or $C_1$–$C_6$-alkylcarbonyl, and n represents 2, except far 2-(phenylsulfanyl)-5,6-dihydro-4H-1,3-thiazine, 2-[(3-chlorophenyl)sulfanyl]-5,6-dihydro-4H-1,3-thiazine, 2-[(4-chlorophenyl)sulfanyl]-5,6-dihydro-4H-1,3-thiazine, 2-(methylsulfany)-5,6-dihydro-4H-1,3-thiazine, 2-[(4-methoxyphenyl)sulfanyl]-5,6-dihydro-4H-1,3-thiazine, 2-[(4-methyhenyl)sulfanyl]-5,6-dihyro-4H-1,3-thiazine, 2-(ethylsulfanyl)-5,6-dihydro-4H-1,3-thiazine, 2-[(4-nitrophenyl)sulfanyl]-5,6-dihydro-4H-1,3-thiazine, 2-[(3,4-dichlorophenyl)sulfanyl]-5,6-dihydro-4H-1,3-thiazine, 2-[(2chlorophenyl)sulfanyl]-5,6-dihydro-4H-1,3-thiazine, 2-(5,6-dihydro-4H-1,3-thiazin-2-ylsulfanyl)-1-phenylethanone, 2-{[3-(trifluoromethyl)-1,2,4-thiadiazol-5-yl]sulfanyl}-5,6-dihydro-4H-1,3-thiazine, 2-[(2,4-dichlorophenyl)sulfanyl]-5,6-dihydro-4H-1,3-thiazine, 2-[(4-bromophenyl)sulfanyl]-5,6-dihydro-4H-1,3-thiazine, 2-[(2,6-dichlorophenyl)sulfanyl]-5,6-dihydro-4H-1,3-thiazine, 2-[(3,5-dichlorophenyl)sulfanyl]-5,6-dihydro-4H-1,3-thiazine, 2-[(3-methylphenyl)sulfanyl]-5,6-dihydro-4H-1,3-thiazine, 2-[(2-methylphenyl)sulfanyl]-5,6-dihydro-4H-1,3-thiazine, 4-(5,6 -dihydro-4H-1,3-thiazin-2-ylsulfanyl)-N,N-dimethylaniline, 2-[(4-fluorophenyl)sulfanyl]-5,6dihydro-4H -1,3-thiazine, 2-[(4-tert-butylpheny)sulfanyl]-5,6-dihydro-4H-1,3-thiazine 2-[(4-chloro-2-methylphenyl)sulfanyl]-5,6-dihydro-4H-1,3-thiazine 2-[(pentachlorophenyl)sulfanyl]-5,6-dihydro-4H-1,3-thiazine 2-[(2,4,6-trichlorophenyl)sulfanyl]-5,6-dihydro-4H-1,3-thiazine, 2-[(2,5-dichlorophenyl)sulfanyl]-5,6-dihydro-4H1,3-thiazine and 2-[(4-iodophenyl)sulfanyl]-5,6-dihydro-4H-1,3-thiazine.

5. A process for preparing a compound of the formula (I)

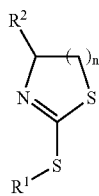

(I)

wherein $R^1$ represents hydrogen or represents phenyl which is optionally mono- or polysubstituted by identical or different substituents from the group consisting of halogen, $C_1$–$C_6$-alkyl, $C_3$–$C_8$-cycloalkyl, $C_1$–$C_6$-haloalkyl, $C_1$–$C_6$-haloalkoxy, $C_1$–$C_6$-alkoxy, nitro, nitrile, hydroxyl, amino, phenoxy, phenyl and di-$C_1$–$C_6$-alkylamino, $R^2$ represents hydrogen, $C_1$–$C_6$-alkoxycarbonyl or $C_1$–$C_6$-alkylcarbonyl, wherein R1 and R2 cannot both be hydrogen, and n represents 2, except for 2-(phenylsulfanyl)-5,6-dihydro-4H-1,3-thiazine, 2-[(3-chlorophenyl)sulfanyl]-5,6-dihydro-4H-1,3-thiazine, 2-[(4-chlorophenyl)sulfanyl]-5,6-dihydro-4H-1,3-thiazine, 2-(methylsulfanyl)-5,6-dihydro-4H-1,3-thiazine, 2-[(4-methoxyphenyl)sulfanyl]-5,6-dihydro-4H-1,3-thiazine, 2-[(4-methylphenyl)sulfanyl]-5,6-dihydro-4H-1,3-thiazine, 2-(ethylsulfanyl)-5,6-dihydro-4H-1,3-thiazine, 2-[(4-nitrophenyl)sulfanyl]-5,6-dihydro-4H-1,3-thiazine, 2-[(3,4-dichlorophenyl)sulfanyl]-5,6-dihydro-4H-1,3-thiazine, 2-[(2-chlorophenyl)sulfanyl]-5,6-dihydro-4H-1,3-thiazine, 2-(5,6-dihydro-4H-1,3-thiazin-2-ylsulfanyl)-1-phenylethanone, 2-{[3-(trifluoromethyl)-1,2,4-thiadiazol-5-yl]sulfanyl}-5,6-dihydro-4H-1,3-thiazine, 2-[(2,4-dichlorophenyl)sulfanyl]-5,6-dihydro-4H-1,3-thiazine, 2-[(4-bromophenyl)sulfanyl]-5,6-dihydro-4H-1,3-thiazine, 2-[(2,6-dichlorophenyl)sulfanyl]-5,6-dihydro-4H-1,3-thiazine, 2-[(3,5-dichlorophenyl)sulfanyl]-5,6-dihydro-4H-1,3-thiazine, 2-[(3-methylphenyl)sulfanyl]-5,6-dihydro-4H-1,3-thiazine, 2-[(2-methylphenyl)sulfanyl]-5,6-dihydro-4H-1,3-thiazine, 4-(5,6-dihydro-4H-1,3-thiazin-2-ylsulfanyl)-N,N-dimethylaniline, 2-[(4-fluorophenyl)sulfanyl]5,6dihydro-4H-1,3-thiazine, 2-[(4-tet-butylphenyl)sulfanyl]-5,6-dihydro-4H-1,3-thiazine 2-[(4-chloro-2-methylphenyl)sulfanyl]5,6-dihydro-4H-1,3-thiazine 2-[(pentachlorophenyl)sulfanyl]5,6-dihydro-4H,1,3-thiazine 2-[(2,4,6-trichloropheny)sulfanyl]-5,6-dihydro-4H-1,3-thiazine, 2-[(2,5-dichlorophenyl)sulfanyl]5,6-dihydro-4H-1,3-thiazine and 2-[(4-iodophenyl)sulfanyl]-5,6dihydro-4H-1,3-thiazine, wherein the process comprises reacting:
(1) a mercaptan of the formula (II) or a salt thereof

 (II)

wherein
R¹ has the above given meaning with
(2) an isothiocyanate of the general formula (IV)

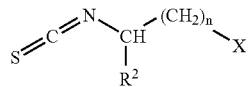 (IV)

wherein
R² has the above given meaning,
n is 2, and
X represents halogen or a leaving group.

6. The process according to claim 5, wherein the process is carried out in the presence of a diluent or in the presence of an acid binder, or both in the presence of a diluent and an acid binder.

7. A microbicidal composition for protecting an industrial material selected from glues, sizes, paper and board, textiles, leather, wood, wooden materials, paints, synthetic articles, cooling lubricants and combinations thereof, against attack and destruction by a microorganism,
comprising at least one compound of a compound of the formula (I)

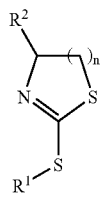 (I)

wherein
R1 represents hydrogen or in each case optionally substituted alkyl, alkenyl, alkinyl, cycloalkyl, aryl or heterocyclyl,
R2 represents hydrogen, alkoxycarbonyl or alkylcarbonyl and
n represents 2,
and at least one solvent or diluent.

8. The composition of claim 7, wherein the composition further comprises a processing auxiliary and an additional antimicrobially active substance component.

9. The compositions according to claim 8, wherein the additional antimicrobially active substance component is selected from the group consisting of fungicides, bactericides, acaricides, nematicides, algicides, insecticides, and combinations thereof.

* * * * *